US006462087B1

(12) United States Patent
Morinaga et al.

(10) Patent No.: US 6,462,087 B1
(45) Date of Patent: Oct. 8, 2002

(54) ANTI-TUMOR COMPOSITION

(75) Inventors: Yoshihiro Morinaga; Yukio Nihei; Yasuyo Suga; Manabu Suzuki; Kazuo Ohishi; Akira Okano, all of Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 09/678,406

(22) Filed: Oct. 3, 2000

Related U.S. Application Data

(63) Continuation of application No. PCT/JP99/01633, filed on Mar. 29, 1999.

(30) Foreign Application Priority Data

Apr. 3, 1998 (JP) ............................................ 10-108708
Aug. 14, 1998 (JP) ............................................ 10-229843

(51) Int. Cl.⁷ ........................ A16K 31/17; A16K 33/24
(52) U.S. Cl. ...................................... 514/598; 424/649
(58) Field of Search ........................... 514/598; 424/649

(56) References Cited

U.S. PATENT DOCUMENTS 5,674,906 A * 10/1997 Hatanaka et al. ........... 514/626

OTHER PUBLICATIONS

Tashiro, Nippon Kaglku Kaishi (1988), (4), 684–90 Abstract Only.*

"Enhancing and Inhibitory Effects of Some Stilbene and Steroid Compounds on Induction of Hepatoma in Rats Fed 3'–Methyl–4–(Dimethylamino)Azobenzene" Gann, 69, no. 3, pp. 375–382, Jun. 1978 (Chiba).

"Anti–Leukaemic Compounds Derived From Stilbenes in *Picea abies* Bark", Phytochemistry, vol. 33, No. 4, 1993 pp. 813–816.

American Assosiation for Cancer Research, Eighty–Ninth Annual Meeting, Proceedings, Mar. 28–Apr. 1, 1998, New Orleans, LA., vol. 39 –Mar. 1998.*

* cited by examiner

*Primary Examiner*—Jerome D. Goldberg
(74) *Attorney, Agent, or Firm*—Oblon, Spivak, McClelland, Maier & Neustadt, P.C.

(57) ABSTRACT

The present invention provides composition having as active ingredients a stilbene derivative and a platinum coordination compound which is highly efficacious and highly safe for treating tumors, particularly for the treatment of solid or malignant tumors and thus methods of cancer and tumor treatment using the composition are also provided.

8 Claims, No Drawings

ANTI-TUMOR COMPOSITION

CONTINUING DATA

This application is a continuation of PCT/JP99/01633, filed Mar. 29, 1999, the entire contents of which are herein incorporated by reference.

BACKGROUND OF THE INVENTION

1. Field of the Invention

This invention relates to a novel antitumor or anti-neoplastic agent, composition and treatment. More particularly, it is directed to compositions comprising a stilbene derivative and a platinum coordination compound, such as the drug Cisplatin. Such compositions have been discovered to be safe and highly effective anti-neoplastic agents and are thus useful for the prevention, amelioration, treatment or cure of neoplasms, cancer, and tumors, particularly malignant or solid tumors. These compositions may optionally include other therapeutic compounds or agents. The invention is also directed to methods of using a composition comprising a stilbene derivative and a platinum coordination compound, and to methods of co-administration of these compounds to prevent, ameliorate, treat, or cure neoplasms, cancer or tumors.

2. Discussion of the Background

There is a pronounced need for safe and more efficacious anti-tumor agents. While a wide variety of chemotherapeutic agents are presently used for the treatment, suppression and prevention of tumors, tumors may develop a resistance to such agents, especially highly malignant or solid tumors. Thus, tumor relapse is a common problem. Also, existing agents, even if effective, may be inconvenient to administer in effective dosages and have inadequate therapeutic indexes. Thus, patients may suffer from pain and other side-effects of their administration, especially from the administration of high doses of anti-tumor agents with relatively low potencies.

Platinum coordination compounds, such as Cisplatin and other diamino-platinum complexes, have been widely used in humans as chemotherapeutic drugs. The platinum coordination compound used in the present invention is such a compound which gives platinum preferably in an ionic form, and preferably is a compound exhibiting substantial anti-tumor activity, more preferably a platinum coordination compound exhibiting tumor cell proliferation preventative or inhibiting properties. Many platinum coordination compounds used in the present invention are commercially available or may be manufactured by known or routinely used techniques. However, these compounds are not therapeutically effective for all patients or all types of tumors. For instance, numerous attempts have been made to improve Cisplatin-based therapy by using Cisplatin in combination with other drugs. Although some attempts have achieved improvements in efficacy, these compositions were not sufficiently effective in treating tumors, reducing tumor burden, or in relieving the pain and other complications suffered by tumor patients. Thus, there is a need to discover other agents which together with a platinum coordination compound would be more efficacious in treating tumors.

Cisplatin or cis-diamminedichloroplatinum (II) has been successfully used for long as a chemotherapeutic drug in the therapy of various malignant tumors in the human being.

More recently, other diamino-platinum complexes have shown efficacy as chemotherapeutic drugs in curing various malignant tumors in the human being. Examples of the diamino-platinum complexes may be spiroplatinum and carboplatinum.

Cisplatin and other diamino-platinum complexes have been widely used as chemotherapeutic drugs in the humans. However, these are not therapeutically efficient for all patients or all sorts of tumors. In expectation of possibly increasing therapeutic efficacy, numerous attempts have been made towards using Cisplatin in combination with Vindesine, see Garalla, R. J. etal., Ann. Intern. Med. 95: 414–420 (1980) or using Cisplatin in combination with VP-16, see Congeval, E. et al., Cancer, 51: 2751–2756 (1982). Although such combined application has achieved certain improvement in the efficacy ratio, it cannot be said that the tumor burden or pains of tumor-bearing patients has been completely relieved by these measures.

Stilbene derivatives which have cis-stilbene as a fundamental skeleton, are known to strongly inhibit mitosis and cause cytotoxicity. However, existing stilbene derivatives have not been available or practical as pharmaceutical agents for a number of reasons, including their low solubilities in water.

Recently, certain stilbene derivatives which inhibit tubulin polymerization and having improved solubility in water have been investigated, for instance, the phosphorylated pro-drug Combretastatin-A4, see U.S. Pat. No. 5,561,122. Other stilbene derivatives having improved solubility in water have been proposed as drugs, such as those of the present Assignee as described for instance in Japanese Pat. Kokai Publications JP-A-7-228558 and JP-A-8-301831.While such stilbene derivatives are promising, alone they may exert insufficient anti-tumor activity. Thus, it is desired to enhance the antitumor efficacy and safety of compositions containing stilbene derivatives.

BRIEF SUMMARY OF THE INVENTION

It is an object of the present invention to develop a superior antitumor agent, specifically, to develop a pharmaceutical preparation which improves the efficacy of a stilbene derivative and, in particular, to develop and provide an antitumor agent exhibiting superior safety and anti-tumor efficacy for reducing the severity, preventing, treating or curing tumors and other neoplasms, particularly solid or highly malignant tumors.

The present inventors have persistently and methodically conducted research with the above objectives in mind in order to overcome the recognized problems of the prior art compounds and therapies. Through these efforts, it has been discovered that a stilbene derivative when administered together with a platinum coordination compound, such as Cisplatin, provide enhanced or synergistic anti-neoplastic or anti-tumor effects and significantly enhance the tumor-inhibiting properties of either or both compounds.

Addition of a stilbene derivative to a therapeutic platinum coordination compound can provide superior anti-neoplastic or anti-tumor effects compared to combinations of other chemotherapeutic drugs with a platinum coordination compound, such as Cisplatin. Such stilbene-containing compositions thus provide a chemotherapeutic drug higher in efficacy useful to treat tumor or cancer patients. For instance, enhanced or synergistic effects are achieved by employing a stilbene derivative in combination with platinum coordination compound, such as Cisplatin. Such compositions are used to more efficaciously and safely to treat or cure tumors and solid cancers.

The present inventors have found that, by combining a stilbene derivative, most preferably one having in-vitro tubulin polymerization inhibiting activity with a platinum coordination compound such as Cisplatin, it is possible to completely cure tumors and prevent decreases in body weight. For instance, it is demonstrated that the present invention cures mice of malignant engrafted tumors. These studies show that the inventive compositions are highly effective chemotherapeutic agents against cancer and tumors, and thus may find successful application for treating or curing various solid cancers or tumors, such as pulmonary or lung cancer.

Vincristine, Vindesine, and Vinblastine are examples of currently known therapeutic agents having tubulin polymerization inhibiting activities. These agents are used for treatment of solid cancers in multi-drug or polypharmacy therapeutic approaches. They may be used in combination with drugs such as Cisplatin. However, complete curing of tumors in mice has not been observed after simultaneous administration of Vindesine and Cisplatin. Further, the combination of Vindesine and Cisplatin is shown to result in significant decreases in body weight, and thus such combinations may be toxic and unsafe.

On the other hand, the inventive combination of Cisplatin and a stilbene derivative results in complete curing of tumors in mice and this effect is attributed to -the combined, enhanced or synergistic action of the compositions of the present invention. Further, combinations of a stilbene derivative and Cisplatin have improved safety as they do not cause significant decreases in weight. For instance, a composition comprising Cisplatin and the compound shown by the following structural formula (3):

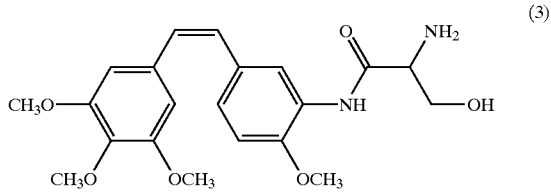

(3)

did not cause significant decreases in body weight compared to the combination of Cisplatin with other anti-tumor agents, such as Vindesine, see Table 3 below.

These results are compelling evidence of the highly efficacious properties of the inventive combination in treating tumors in animals, preferably mammals, and most preferably human cancer patients compared to compositions containing Cisplatin and other (non-stilbene) chemotherapeutic drugs. Thus, the present invention provides an improved anti-neoplastic or antitumor agent, especially for cancer chemotherapy, and provides a means for relieving patients from tumor burdens, as well as safely reducing the side-effects of cancer therapy. That is, the present invention provides a high potency antitumor effect thus ii providing a means for reducing the overall dosages of antitumor agents administered, and thus providing reductions in toxicity and side-effects.

Accordingly, the present invention using the combination of a stilbene derivative and a platinum coordination compound provides a novel and highly efficacious compositions and methods for the treatment of neoplastic diseases, especially tumors.

DETAILED DESCRIPTION OF THE INVENTION

As discussed above, the present invention is directed to an antitumor agent comprising al least one stilbene derivative and at least one platinum coordination compound. The stilbene derivative and platinum coordination compound may be combined together in one composition, or separately compounded and then administered together. For instance, the claimed invention may comprise a kit comprising a stilbene derivative and a platinum coordination compound as well as equipment and supplies for the administration of these compounds as well as instructions for use.

The present invention also encompasses compositions comprising more than one type of stilbene derivative or more than one type of platinum coordination compound.

Combinations of stilbene derivatives and platinum coordination compounds with other pharmacological agents, anti-tumor drugs or assistant anti-tumor agents are also encompassed by the invention.

The invention also encompasses methods of treatment involving the coadministration or sequential administration of a stilbene derivative and platinum coordination compound.

All sorts of neoplasms and tumors occurring in animals, especially mammals, and most preferably humans, may be treated using the compositions and methods of the present invention. Most preferably, the antitumor agent and methods of the present invention may be used for inhibiting the growth and proliferation of tumor cells in a human being.

There is no particular limitation to the form of administration of the antitumor agent. The platinum coordination compound can be routinely administered parenterally, and the stilbene derivative can also be administered parenterally. However, the present invention also encompasses methods involving a combination of distinct methods or routes of administration. For instance, the stilbene derivative can be administered in a different form and route than the platinum coordination compound, or according to a separate dosage schedule.

Preferably, the stilbene derivative used in the present invention has cis-stilbene as a fundamental skeleton and exhibits in vitro tubulin polymerization inhibiting activity and/or an antitumor activity. Tumor cell proliferation inhibiting activity is the preferred type of anti-tumor activity. Known compounds, as well as stilbene compounds which will be found in future, are included in the stilbene derivatives in the present invention provided that such newly found compounds are classed as stilbene derivatives. The stilbene derivatives of the present invention also include bioprecursors or compounds which may be converted in an animal body into a stilbene derivative. Any suitable or pharmaceutically allowable derivatives, such as salts, esters, solvates (salvation products) such as hydrates thereof, may be used as the stilbene derivatives in the present invention. Preferably, such derivatives exhibit significant antitumor activity when used in vivo. The present compositions may also be used in vitro or in methods of ex vivo treatment.

Among representative stilbene derivatives, having the cis-stilbene as a fundamental skeleton, there are preferably compounds represented by the following formulas (1) and (2):

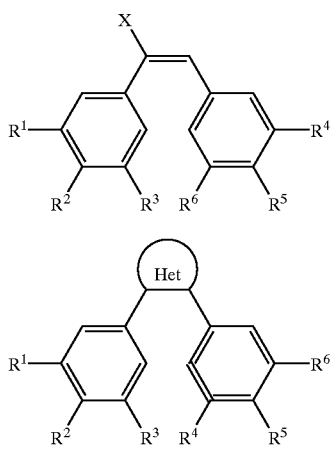

(1)

(2)

and corresponding salt, hydrates and solvates (solvation products), and especially pharmaceutically acceptable forms thereof.

In the adove formulas, $R^1$, $R^2$ and $R^3$ independetly donate lower alkoxy groups, $R^4$, $R^5$ and $R^6$ independently donate any substitute of a hydrogen atom, a halogen atom (fluorine, chlorine atoms, etc.), a nitro group, a hydroxyl group, a lower alkoxy group, a phosphoric acid ester (a substitute formed on phosphoric acid esterification with a hydroxyl group: —$OPO_3H_2$, hereinafter the same), a phosphoric acid amide (a substitute formed on phosphoric acid amidation with an amino group: —$NHPO_3H_2$, hereinafter the same), an amino lower alkoxy group, a lower alkyl amino lower alkoxy group, a di-lower alkyl amino lower alkoxy group, a mercapto group, a lower alkyl thio group, an amino group, a lower alkyl amino group, a di-lower alkyl amino group, a lower alkyl group, an amino lower alkyl group, a trifluoro methyl group, a lower alkanoyl group, a lower alkanoyl amino group and an amino acid acylamino group, X denotes a hydrogen atom or a nitrile group, and Het denotes a heterocyclic ring.

The number of carbon atoms in the above described lower alkyl group and the lower alkoxy group is from 1 to 5 and the number of carbon atoms in the lower alkanoyl group is from 2 to 6.

The amino acid acyl group in the amino acid acylamino group is an acyl group derived from an amino acid. The amino acids may be α-amino acids, β-amino acids and γ-amino acids. Examples of preferred amino acids include glycine, alanine, leucine, serine, lysine, glutamic acid, aspartic acid, threonine, valine, isoleucine, ornithine, glutamine, aspargine, tyrosine, phenylalanine, cysteine, methionine, arginine, β-alanine, tryptophan, proline, histadine, etc. The amino acids may be of the L-, D- or DL-form, preferably the L-form. In particular, threonine and serine are preferred in view of their pharmaceutical effects and safety.

The heterocyclic rings may be, for example, tetrazole ring, thiazole ring and the like. If the heterocyclic ring is a thiazole ring, it may have a substitute of a lower alkyl group, an amino group, a mono-lower alkyl amino group, a di-lower alkyl amino group, a hydrazino group, a halogen atom, such as fluorine and chlorine atom, and a lower alkoxy group. The number of carbon atoms in the lower alkyl group and the lower alkoxy group is 1 to 5.

As described above, the stilbene derivative in the present invention is a compound having a cis-stilbene skeleton in its structure and which exhibits a tubulin polymerization inhibiting activity and/or an antitumor activity. The stilbene derivative may be, for example Combretastatine-A4, or a tumor proliferation inhibitive stilbene derivative, disclosed in prior art publications, such as patent publications, e.g. U.S. Pat. Nos. 4,996,237, 5,561,122 and 5,430,062, Japanese Patent Kokai Publications JP-A-7-228558, JP-A-8-301831 and JP-A-8-301831 and JP-A-10-81673, corresponding to Japanese patent Application Serial No. 236603/1996 filed by the present Applicant on Sept. 6, 1996. The prior art stilbene derivatives, described in these patent publications, can be used as the stilbene derivatives of the present invention, insofar as the prior art stilbene derivatives conform with the above definition of the stilbene derivatives in the present invention. In addition, all the contents of the prior art patent publications describing stilbene derivatives are incorporated herein by reference.

The above-mentioned stilbene derivatives may be manufactured by any routine technique including the methods disclosed in the above-mentioned publications. It is noted that future stilbene derivatives may be manufactured and used for the present invention in the same manner as described above.

Among the stilbene derivatives of the present invention, there are salts, esters, and other derivatives of stilbene, and derivatives which may be converted in vivo into stilbene derivatives, insofar as the stilbene derivatives manifest the above-mentioned objective activities in an animal body.

As the stilbene derivative used in the present invention, a compound represented by the following formula (1) is preferred:

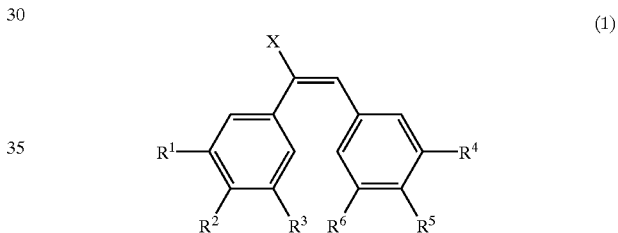

(1)

where $R^1$, $R^2$, $R^3$ and $R^4$ denote a methoxy group, $R^4$ is an amino group or an amino acid acylamino group and $R^6$ and X are hydrogen.

Particularly preferred among the compounds represented by the above formula (1), is a compound represented by the following formula (3), also referred to as Compound (3) below:

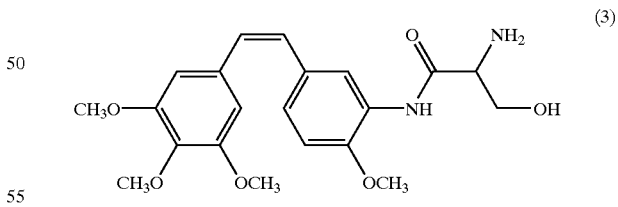

(3)

Compound (3) is (Z)-1-(3-amino-4-methoxyphenyl)-2-(3,4,5-trimethoxyphenyl)-ethene-L-serine amide, and is soluble in water. Compound (3) may be in the form of a salt, for example, hydrochloride, acetate, methanesulfonate and the like.

The manufacture of Compound (3), which may be in the form of the pharmaceutically acceptable salts, hydrates and solvates, and the manufacture of oral and/or parenteral pharmaceutical compositions containing Compound (3), as well as inert pharmaceutically acceptable carrier(s) and/or diluent(s), are extensively disclosed in Japanese Pat. Kokai Publication JP-A-8-301831, which is specifically incorporated by reference.

The platinum coordination compound used in the present invention is a compound which provides platinum, preferably in an ionic form, and also exhibits antitumor activity. More preferably, the platinum coordination compound exhibits tumor cell proliferation preventative (inhibiting) properties.

Specific examples of platinum coordination compounds, employed in the present invention, preferably include Cisplatin, cis-diamminediaquoplatinum (II)-ion, chloro (diethylenetriamine)-platinum (II) chloride, dichloro (ethylenediamine)platinum (II), diammine(1,1-cyclobutanedicarboxylato)platinum (II) (carboplatin), Spiroplatin, Iproplatin, diammine (2-ethylmalonato)-platinum (II), ethylenediamminemalonatoplatinum (II), aqua(1,2-diaminodichlohexane)sulfatoplatinum (II), (1,2-diaminocyclohexane) malonate platinum (II), (4-caroxyphthalato)(1,2-diaminocyclohexane)-platinum (II), (1,2-diaminocyclohexane) (isocitrato)platinum (II), (1,2-diaminocyclohexane)cis (pyruvato)platinum (II), (1,2-diaminocyclohexane)oxalateplatinum (II), Ormaplatin and Tetraplatin.

Certain explanations will be hereinafter made as to a platinum complex, included in the platinum coordination compound according to the present invention, as a chemotherapeutic drug.

As the platinum coordination compounds used in the present invention, there are those compounds already known as the chemotherapeutic drugs, see Tamura, T. etal., Jpn J. Clin. Oncol. vol.18 (1):27 (1988) and Fukuda, M. etal., Cancer Chemother. Pharmacol., vol.26: 393 (1990).

It is necessary to increase the efficacy of the tumor proliferation suppressing activity of Cisplatin and other diamino-platinum complexes in order to reduce the tumor burden and help relieve the patient of tumor-associated pain.

Among the platinum coordination compounds used for the present invention, Cisplatin, Carboplatin and Nedaplatin are preferred due to their curative effects. Although the compound "Cisplatin", which means cis-diamminedichloroplatinum (II), may be manufactured by prior art techniques, it is also available commercially. For example, Cisplatin may be obtained, as a powder for constituting with water, an aseptic physiological saline water or other suitable excipient, under the trade name of Platinol (Registered Trademark) from Bristol Myers-Squibb Co. or under the trade name of "randa Inj." from NIPPON KAYAKU CO., LTD.

Other platinum coordination compounds used in the present invention are commercially available or may be manufactured by known or routinely used techniques. Insofar as the platinum coordination compounds come within the definition therefor of the present invention, the platinum coordination may be purchased or manufactured by manufacturing methods which will be developed in future.

When the antitumor agent of the present invention is to be used, stilbene derivatives in an amount sufficient to inhibit tumor proliferation may be combined with platinum coordination compounds, and administered to a subject animal, preferably a mammal, and more preferably a human being, in need of curing, alleviation or prevention of tumors, especially a human being suffering from tumor cell proliferation, to inhibit tumor cell proliferation.

As described above, the two types of such efficacious ingredients in the present invention may be combined in a pharmaceutical preparation with the objective of obtaining an enhanced anti-tumor effect. For instance, a preferred embodiment of the present invention is to use compound (3) in an amount effective to inhibit tumor cell proliferation in combination with Cisplatin to inhibit tumor cell proliferation.

Moreover, a pharmaceutical preparation containing one of the two efficacious ingredients is also encompassed by the present invention, if such pharmaceutical preparation has the objective of being used in combination with the pharmaceutical preparation containing the other efficacious ingredient in the present invention. This pharmaceutical preparation may contained ,for example, as one component in a therapeutic kit.

The inhibition of tumor cell proliferation means inhibition of proliferation of the tumor cells sensitive to therapy including administration of an effective amount of the stilbene derivatives, such as compound (3), and the platinum coordination compounds, such as Cisplatin, to, for example, a human being suffering from tumor cell proliferation. In an acceptable case, this administration suppresses tumor cell proliferation or diminishes the measurable tumor size. In an optimum case, the tumor undergoes complete regression.

As described above, there is no particular limitation to the method of administering the antitumor agent of the present invention to the human being, such that it may be administered orally or parenterally, for instance, intravenously, or by a subcutaneous or intramuscular route. For prompt efficacy, parenteral administration, such as by intravenous and subcutaneous administration, or by infusion, etc. is preferred.

In the method for administering the pharmaceutical preparation according to the present invention, the stilbene derivative may be administered simultaneously with the platinum coordination compound or the two may be sequentially administered in an optional order. The practically desirable method and sequence for administration are varied depending on the individual preparation of the stilbene derivative used, such as the compound (3), individual preparation of the platinum coordination compound in use, such as Cisplatin, individual tumor cells being cured, and the individual subjects being treated. The optimum method and sequence for administration of the stilbene derivative and the platinum coordination compound under preset given conditions may be suitably selected by those skilled in the art with the aid of the routine technique and the information contained in the present specification.

Curative and tumor-inhibiting amounts of stilbene derivatives in combination with platinum coordination compounds may be calculated by those with skill in the art based on the present disclosure. A curative unit will inhibit proliferation of tumor cells sensitive to these compounds in the human being suffering from tumor cell proliferation. The practically to desirable curative unit is varied depending on the individual dosage forms of the stilbene derivative used, such as compound (3), individual dosage forms of the platinum coordination compound, such as Cisplatin, individual tumor cells being cured and the individual subjects being treated. The optimum curative units for preset given conditions may be suitably selected by those skilled in the art with the aid of the curative test units and the information contained in the present specification.

When administering the antitumor agent of the present invention, the administration schedule for the platinum coordination compound is preferably determined by setting approximately 1 to 500 mg/m$^2$ of the body surface area per curative unit as a reference. When using Cisplatin and compound (3), these may be administered simultaneously, Cisplatin may be administered either before or after the administration of compound (3); Alternatively, these compounds may be used in combination. The preferred amount of Cisplatin for administration is approximately 10 to 100 mg/M² of the body surface area per day. It is preferably administered simultaneously along with curative units of Compound (3) continuously for one to five days at a time.

The platinum coordination compound in an infusion form is preferably infused once or twice a week. This weekly infusion is preferably repeated several times unless contraindicated by the appearance of undesirable side effect actions such as nephrotoxicity and neurotoxicity. It is possible to use other conventionally used techniques simultaneously with the administration of the platinum compound, such as Cisplatin or the other platinum coordination compound.

The antitumor agent of the present invention may comprise a pharmaceutical preparation comprising at least the stilbene derivative and the platinum coordination compound as described above, such that the two active ingredients may be contained as a mixture in the pharmaceutical preparation. However, the two active ingredients in the present invention may also be contained separately in distinct pharmaceutical preparations used in combination. It is noted that such a pharmaceutical preparation containing other agents (third and fourth medical ingredients and so on) such as other antitumor agents, may naturally be encompassed by the present invention, insofar as the effective ingredients used in the present invention are contained in the pharmaceutical preparation. Moreover, it is possible for carriers, diluents and other substances, pharmaceutically acceptable for any of the pharmaceutical preparations in the present invention (a sole pharmaceutical preparation containing both ingredients in the present invention and separate pharmaceutical preparations separately each containing one of the two ingredients for use in combination) to be contained in the antitumor agent of the present invention.

As the suitable pharmaceutically acceptable carriers and diluents, used in the antitumor agent of the present invention, those carriers, diluents and excipients and the like known to those skilled in the art of preparation of pharmaceutical preparations, may be used as appropriate. Such carriers are disclosed in, for example, Japanese Patent Kokai Publication JP-A-8-301831 and the other aforementioned prior art publications.

The antitumor agent of the present invention may be suitably applied parenterally, as discussed above. In this case, the antitumor agent is prepared into an intravenous infusion or injection, along with pharmaceutically acceptable carriers by various methods known to those skilled in the art. Preferably, the pharmaceutical agent is manufactured by a routine technique e.g. in a unit dosage form and in the form of a freeze-dried mixture of two effective ingredients, which is re-prepared in water or another suitable liquid infusion prior to administration.

The ratio of the two ingredients for the pharmaceutical preparation for the antitumor agent of the present invention may be varied in a wide range, depending on a number of factors, such as a desired amount of administration and on the pharmaceutically acceptable carrier in use. The ratios of the stilbene derivative and platinum coordination compound of the present invention for use in a pharmaceutical preparation are for the stilbene derivative approximately 0.01 to 1000 parts by weight, preferably approximately 0.1 to 100 parts by weight, to 1 part by weight of the platinum coordination compound. So, when the pharmaceutical preparation in the present invention containing two active ingredients is to be administered to the patient, it is administered in an amount which will give the above-defined administration range.

If the pharmaceutical preparation is to be administered stepwise, the above-defined administration range can be set as the average ratio for the separate pharmaceutical preparations.

Preferably, 5 to 500 mg of the platinum coordination compound, more preferably 10 to 50 mg as Cisplatin, 0.1 to 10,000 mg of the stilbene derivative and more preferably 1 to 1,000 mg as the compound (3) may be contained for each dosage of the pharmaceutical preparation according to the present invention. It is desirable that mannitol and/or sodium chloride be contained in routine amounts in the pharmaceutical preparation of Cisplatin. The physiological pharmaceutical value of the pharmaceutical composition used as an injection or infusion liquid is suitably adjusted by the content of a buffer well-known in the art.

Having generally described this invention, a further understanding can be obtained by reference to certain specific examples which are provided herein for purposes of illustration only, and are not intended to be limiting unless otherwise specified.

EXAMPLE 1

Antitumor Effect and Safety Tests

A pharmaceutical composition comprising the stilbene derivative of formula (3):

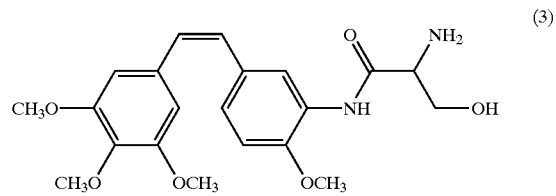

was prepared and used in the tests presented below:

Stilbene derivative of formula (3) as the hydrochloride 10 mg

Physiological saline solution in water: 10 ml

As Cisplatin, a pharmaceutical preparation marketed by NIPPON KAYAKU CO., LTD. under the trade name of "randa Inj." (a preparation containing 0.5 mg of Cisplatin in 1 ml of a solution) was used.

Methodology. 10 mg of a murine colonic tumor, colon 26, was inoculated under the skin of the back of CDF1 mice (day 0). After one week, the tumor was measured to calculate the volume of the tumor and the mice were classified into several groups (each group: n=5) and administration of the stilbene derivative and Cisplatin was started. On days 7, 11 and 15, the tumor-inoculated mice were bolusly injected under the skin of their backs and into their tail veins with 1 mg of the stilbene derivative of formula (3) in 1 ml of physiological saline solution and 0.5 mg of Cisplatin ("randa Inj") in a volume of 1 ml. Control and comparative groups of mice were similarly injected with the other drug combinations described in Table 1. The comparative drug Vindesine is an antitumor drug used in combination with Cisplatin by Garalla et al. VP-16 is also a chemotherapeutic drug which is often used clinically in combination with Cisplatin. The dosages of Cisplatin, VP-16 and Vindesine represent the maximum dosage without death due to the toxicity in the administration schedule in the present example.

As indicated in Table 1 the term [-CDDP] means that Cisplatin was not administered at all. The term [+CDDP] means that Cisplatin was administered in an amount of 5 mg/kg/day. The term [n.d.] means that no testing was performed.

Antitumor effects: Complete regression of the colonic tumor was determined by palpation. Subjects in which the tumor has not been ascertained by palpation on the 60th day were deemed to have their tumors cured completely. These results are shown in Table 1.

TABLE 1

Antitumor Activity Test (1):

| Sample | Amount of Administration mg/kg/day | Number of instances of complete regression of tumors | |
|---|---|---|---|
| | | −CDDP | +CDDP |
| Control | — | 0/5 | 0/5 |
| Compound (3) | 5 | n.d. | 1/5 |
| Compound (3) | 10 | 0/5 | 4/5 |
| Vindesine | 2 | n.d. | 0/5 |
| VP-16 | 30 | 0/5 | 0/5 |

As clearly shown in the results of Table 1, the antitumor agent of the present invention, that is the combination of the stilbene derivative and the platinum coordination compound, produced complete regression of tumors, as compared to a pharmaceutical preparation composed of any one of two ingredients. This shows an enhanced or synergistic effect for these two drugs when used together.

On the other hand, in the pharmaceutical preparation, used clinically in combination with Cisplatin, such as Vindesine or VP-16, the complete tumor regression was not observed.

Safety. The rate of body weight change was used as a measure of safety as significant loss of body weight is undesirable in cancer patients. Body weight change was calculated using the following equation:

Rate of body weight change (%)=[{(body weight−weight of the tumor) at the $21^{st}$ day}−{(body weight−weight of the tumor) at the $7^{th}$ day}]/{body weight−weight of the tumor) at the $7^{th}$ day}×100.

Using the above equation, the rate of body weight change at the 21st day was calculated. The results are shown in Table 2.

TABLE 2

Safety Test (1)

| Sample | Amount of Administration mg/kg/day | Rate of Body Weight Change | |
|---|---|---|---|
| | | −CDDP | +CDDP |
| Control | — | −12.0 | −11.1 |
| Compound (3) | 5 | n.d. | −4.2 |
| Compound (3) | 10 | −7.7 | −1.9 |
| Vindesine | 2 | n.d. | −23.2 |
| VP-16 | 30 | −1.0 | −9.9 |

Concerning the safety aspect, the high rates of body weight loss noted in the groups receiving the combination of Vindesine or VP-16 with the platinum coordination compound, were not observed in test groups receiving the combination of the two ingredients of the present invention, as clearly shown in the results of Table 2.

EXAMPLE 2

Antitumor Effect and Safety Tests (Preparation of Pharmaceutical preparation)

Pharmaceutical preparations for infusion were prepared using stilbene derivatives (4) and (5), shown by the following chemical formulas:

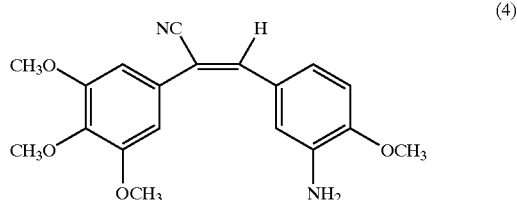

(4)

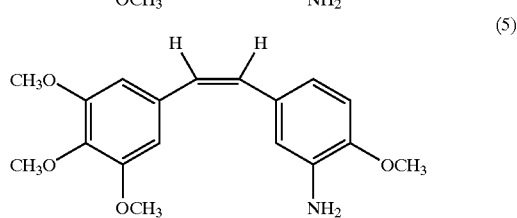

(5)

The following compositions comprising these stilbene derivatives were prepared:

| Compound (4) (as the hydrochloride) | 5 mg; |
|---|---|
| Tween 80 | 0.5 ml; and |
| Physiological saline in water | 9.5 ml. |
| Compound (5) (as the hydrochloride) | 10 mg; |
| Tween 80 | 0.5 ml; and |
| Physiological saline in water | 9.5 ml. |

As in EXAMPLE 1 as described above, the pharmaceutical preparation ("randa Inj.") marketed by NIPPON KAYAKU CO., LTD. (containing 0.5 mg of Cisplatin in 1 ml solution) was used as the Cisplatin. The pharmaceutical preparation ("paraplatin injection") marketed by Bristol Myers-Squibb Co. (containing 10 mg of Carboplatin in 1 ml) was used as the Carboplatin.

Methodology: 10 mg of a colonic tumor of mouse, colon 26 was inoculated under the skin of the back of CDF1 mice (day 0). After one week, the tumor was measured to calculate the volume of the tumor and the mice were classified into several groups (each group: n=5) and administration of the pharmaceutical preparation was started.

Stilbene derivatives of formulas (3), (4) and (5), and Cisplatin and Carboplatin were bolusly injected into the tail vein on the 7th, 11th and 15th days as described in Tables 3 through 6 below.

Antitumor effects: Complete regression of the colonic tumor was determined by palpation. Subjects in which the tumor had not been ascertained by palpation on the 60th day were deemed to have their tumors completely cured. These results are shown in Tables 3 and below.

The terms: [+CBDCA] and [+CDDP] indicate that 50 mg/kg/day of carboplatin or 5 mg/kg/day of cisplatin were administered, respectively. The terms: [−CBDCA] and [−CDDP] indicate that no carboplatin or cisplatin were administered. The dosages of cisplatin and carboplatin denote the maximum dosages without death due to toxicity in the administration schedule in the present embodiment.

TABLE 3

Antitumor Activity Test (2)

| Sample | Amount of Administration mg/kg/day | Number of instances of complete regression of tumors | |
|---|---|---|---|
| | | −CBDCA | +CBDCA |
| Control | — | 0/6 | 0/6 |
| Compound (3) | 20 | 0/6 | 1/6 |

TABLE 4

Antitumor Activity Test (3)

| Sample | Amount of Administration mg/kg/day | Number of instances of complete regression of tumors | |
|---|---|---|---|
| | | −CDDP | +CDDP |
| Control | — | 0/6 | 0/6 |
| Compound (4) | 5 | 0/6 | 4/6 |
| Compound (5) | 20 | 0/6 | 6/6 |

As clearly shown in Tables 3 and 4, the antitumor agent of the present invention comprising a stilbene derivative exhibits superior antitumor activity in combination with a platinum coordination compound.

Safety: The rate of body weight change was used as a measure of safety, as significant loss of body weight is undesirable in cancer patients. Body weight change on the 21$^{st}$ day was calculated using the equation described in Example 1. These results are shown in tables 5 and 6.

TABLE 5

Safety Tests (2)

| Sample | Amount of Administration mg/kg/day | Rate of Body Weight Change | |
|---|---|---|---|
| | | −CBDCA | +CBDCA |
| Control | — | −22.1 | −9.6 |
| Compound (3) | 20 | −7.4 | 1.8 |

TABLE 6

Safety Test (3)

| Sample | Amount of Administration mg/kg/day | Rate of Body Weight Change | |
|---|---|---|---|
| | | −CDDP | +CDDP |
| Control | — | −22.1 | −11.4 |
| Compound (4) | 5 | −7.0 | −13.9 |
| Compound (5) | 20 | −2.1 | −0.3 |

Moreover, concerning the safety aspect, as clearly shown in the results of Tables 5 and 6, outstanding improvement may be noticed by employing the two ingredients of the present invention.

Finally, it may be seen from the results of Tables 1 to 6 that, with the combination of the stilbene derivative and the platinum coordination compound according to the present invention, the efficacy as the antitumor agent can be improved synergistically beyond the expectation by those skilled in the art, such that a practically highly useful antitumor effect can be achieved.

Effects of the Invention

The anti-tumor agent according to the present invention, comprising a stilbene derivative and a platinum coordination compound, such as Cisplatin, in combination or as a mixture, can be used as an anti-tumor agent, especially as a chemotherapeutic drug or agent for cancer treatment. The inventive combination of a stilbene derivative with a platinum coordination compound is highly effective for treatment, suppression, prevention or cure of tumors, especially solid cancers or tumors, such as solid carcinoma. Some of these anti-tumor effects may be attributed to a synergistic effect derived from the combination of the stilbene derivative and platinum coordination compound.

Modifica and other embodiments

Various modifications and variations of the described anti-tumor agents, compositions and methods as well as the concept of the invention will be apparent to those skilled in the art without departing from the scope and spirit of the invention. Although the invention has been described in connection with specific preferred embodiments, it should be understood that the invention as claimed is not intended to be limited to such specific embodiments. Various modifications of the described modes for carrying out the invention which are obvious to those skilled in the medical, biological, chemical or pharmacological arts or related fields are intended to be within the scope of the following claims.

Incorporation by Reference

Each document, patent application or patent publication cited by or referred to in this disclosure is incorporated by reference in its entirety. Any patent document to which this application claims priority is also incorporated by reference in its entirety. Specifically, priority documents JP 10/108708, filed Apr. 3, 1998 and JP 10/229843, filed Aug. 14, 1998 are hereby incorporated by reference.

What is claimed is:

1. A composition comprising synergistic effective amounts of a stilbene derivative represented by formula (3):

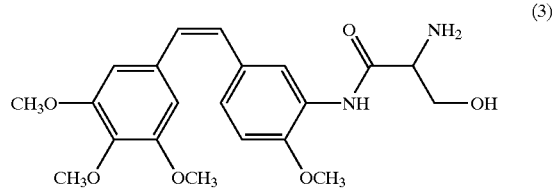

and cis-diaminedichloroplatinum (II).

2. A method for inhibiting cancer or tumor growth comprising administering to a subject in need of treatment the composition of claim 1 in an amount sufficient to inhibit cancer or tumor growth.

3. The method of claim 2, wherein said tumor is a malignant or solid tumor.

4. The method of claim 2, further comprising administering at least one other anti-neoplastic or anti-tumor drug.

5. The method of claim 2, wherein administering comprises intravenous administration or infusion.

6. A method of treating, ameliorating or suppressing a tumor comprising administering to a subject in need of treatment a synergistic effective amount of a stilbene derivative represented by formula (3):

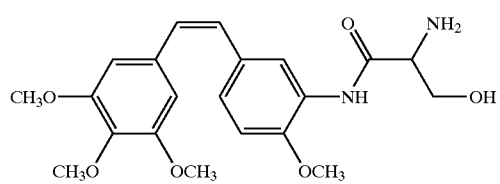

(3)

and cis-diaminedichloroplatinum (II), which is sufficient to treat, ameliorate or suppress the tumor.

7. The method of claim 6, wherein said stilbene derivative and said cis-diaminedichloroplatinum (II) are administered sequentially.

8. The method of claim 6, wherein said stilbene derivative and said cis-diaminedichloroplatinum (II) are administered by separate routes.

* * * * *

UNITED STATES PATENT AND TRADEMARK OFFICE
CERTIFICATE OF CORRECTION

PATENT NO. : 6,462,087 B1  Page 1 of 1
APPLICATION NO. : 09/678406
DATED : October 8, 2002
INVENTOR(S) : Yoshihiro Morinaga et al.

It is certified that error appears in the above-identified patent and that said Letters Patent is hereby corrected as shown below:

At column 14, lines 41 to 42:

"1. A composition comprising synergistic effective amounts of a stilbene derivative represented by formula (3):"

should read:

--1. A composition comprising synergistic effective amounts of a stilbene derivative represented by formula (3), pharmaceutically acceptable salts thereof, pharmaceutically acceptable hydrates thereof, or pharmaceutically acceptable solvates thereof:--

At column 14, lines 64 to 67:

"6. A method of treating, ameliorating or suppressing a tumor comprising administering to a subject in need of treatment a synergistic effective amount of a stilbene derivative represented by formula (3):"

should read:

--6. A method of treating, ameliorating or suppressing a tumor comprising administering to a subject in need of treatment a synergistic effective amount of a stilbene derivative represented by formula (3), pharmaceutically acceptable salts thereof, pharmaceutically acceptable hydrates thereof, or pharmaceutically acceptable solvates thereof:--

Signed and Sealed this

Third Day of August, 2010

David J. Kappos
*Director of the United States Patent and Trademark Office*